(12) United States Patent
Kerboul et al.

(10) Patent No.: US 9,456,828 B2
(45) Date of Patent: Oct. 4, 2016

(54) MEDICAL INSTRUMENT HANDLE

(71) Applicant: Symmetry Medical, Inc., Warsaw, IN (US)

(72) Inventors: Guillaume Kerboul, Gloucestershire (GB); Stuart Weekes, Gloucestershire (GB); Jim Truscott, Gloucestershire (GB)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 231 days.

(21) Appl. No.: 13/745,164

(22) Filed: Jan. 18, 2013

(65) Prior Publication Data

US 2014/0207200 A1 Jul. 24, 2014

(51) Int. Cl.
| | |
|---|---|
| *A61B 17/56* | (2006.01) |
| *A61B 17/16* | (2006.01) |
| *A61F 2/46* | (2006.01) |
| *A61B 17/00* | (2006.01) |

(52) U.S. Cl.
CPC .... *A61B 17/1659* (2013.01); *A61B 2017/0046* (2013.01); *A61B 2090/0813* (2016.02); *A61F 2/4607* (2013.01)

(58) Field of Classification Search
CPC ................ A61B 17/1659; A61B 2017/0046; A61B 2019/4868; A61F 2/4607
USPC ............. 606/99; 24/522, 526, 666; 292/137, 292/283, 302; 70/61
See application file for complete search history.

(56) References Cited

U.S. PATENT DOCUMENTS

| | | | | | |
|---|---|---|---|---|---|
| 2,638,669 | A | * | 5/1953 | Steede | ............................. 30/262 |
| 2,988,797 | A | * | 6/1961 | Gaylord | ........................... 24/606 |
| 3,100,102 | A | * | 8/1963 | De Haan | ............................ 251/9 |
| 3,270,387 | A | * | 9/1966 | Ziegler et al. | ............... 24/122.3 |
| 4,583,270 | A | | 4/1986 | Kenna | |
| 4,601,289 | A | * | 7/1986 | Chiarizzio et al. | ............. 606/85 |

(Continued)

FOREIGN PATENT DOCUMENTS

FR 2 796 261 1/2001

OTHER PUBLICATIONS 5 pages downloaded as publicly available information from Internet on Dec. 7, 2012 pertaining to Wixroyd spring plungers. Two of the pages are labeled at the bottom as "http://www.wixroyd.com/en/page/spring-plungers". Three of the pages are labeled at the bottom as "http://www.wixroyd.com/en/catalog/standard-parts/spring-and-index-plungers/metric-sprin . . . ".

(Continued)

*Primary Examiner* — Zade Coley
(74) *Attorney, Agent, or Firm* — Taylor IP, P.C.

(57) ABSTRACT

A medical instrument handle assembly, for holding a medical instrument configured for preparing a bone to receive an implant, includes: a housing including a housing pin; an elongate arm including a proximal end; a lever subassembly including a lever body and a lever latch, the lever body being pivotally connected to the proximal end of the elongate arm, the lever body and the lever latch being pivotally connected to one another and thereby being selectively positionable relative to one another between a first position and a second position, the first position being when the lever body and the lever latch are clamped about the housing pin, the second position being when the lever body and the lever latch are unclamped relative to the housing pin.

11 Claims, 7 Drawing Sheets

(56) References Cited

U.S. PATENT DOCUMENTS

| | | | | |
|---|---|---|---|---|
| 4,772,013 | A | * | 9/1988 | Tarlow, Jr. ............ A63B 21/153 482/111 |
| 5,089,003 | A | * | 2/1992 | Fallin ................. A61B 17/1659 606/53 |
| D326,912 | S | | 6/1992 | Wasilewski |
| 5,179,783 | A | * | 1/1993 | Melter ............................. 30/262 |
| 5,190,549 | A | | 3/1993 | Miller et al. |
| 5,190,550 | A | | 3/1993 | Miller et al. |
| 5,324,293 | A | | 6/1994 | Rehmann |
| 5,350,381 | A | | 9/1994 | Melton |
| 5,377,412 | A | * | 1/1995 | Schofield et al. .............. 30/262 |
| 5,443,471 | A | | 8/1995 | Swajger |
| 5,531,750 | A | * | 7/1996 | Even-Esh ...................... 606/79 |
| 6,205,884 | B1 | * | 3/2001 | Foley et al. ..................... 74/544 |
| 6,238,435 | B1 | | 5/2001 | Meulink et al. |
| 6,301,787 | B2 | * | 10/2001 | Mock ............................. 30/262 |
| 6,336,272 | B1 | * | 1/2002 | Lee ................................ 30/262 |
| 6,478,801 | B1 | | 11/2002 | Ralph et al. |
| 6,663,636 | B1 | * | 12/2003 | Lin ................................ 606/87 |
| D549,328 | S | | 8/2007 | Aparici et al. |
| 7,621,921 | B2 | * | 11/2009 | Parker ............................ 606/91 |
| 7,946,141 | B2 | * | 5/2011 | Ng et al. ......................... 70/21 |
| 7,976,548 | B2 | | 7/2011 | Burgi et al. |
| 2001/0002515 | A1 | * | 6/2001 | Mock ............................. 30/254 |
| 2007/0167952 | A1 | * | 7/2007 | Burgi et al. .................... 606/99 |
| 2010/0331902 | A1 | | 12/2010 | Biegun |
| 2011/0152954 | A1 | | 6/2011 | Nelson et al. |
| 2012/0059359 | A1 | * | 3/2012 | Burgi ............................. 606/1 |
| 2012/0071862 | A1 | | 3/2012 | Burgi |
| 2012/0083769 | A1 | | 4/2012 | Burgi et al. |

OTHER PUBLICATIONS 1 page document entitled "Broach Handles" by Greatbatch Medical. Document was downloaded as a publicly available document from Internet prior to Jan. 18, 2013.

Office Action dated Mar. 4, 2003 in U.S. Appl. No. 10/095,063 (5 pages).

Document entitled, "Exhibit A" (4 pages), shows devices which were known to others in the United States prior to Jan. 18, 2013.

European Search Report dated Mar. 11, 2014 for European Application No. EP 14 15 0595 (6 pages).

* cited by examiner

MEDICAL INSTRUMENT HANDLE

BACKGROUND OF THE INVENTION

1. Field of the Invention

The present invention relates to medical tool holding devices, and, more particularly, to medical instrument handles such as broach or rasp handles.

2. Description of the Related Art

Total hip replacement involving the use of a hip stem prosthesis requires that the proximal internal geometry of the femur be prepared to receive the hip stem. This involves the removal of the cancellous tissue contained in the proximal femur in order to present a geometry closely approximating that of the hip stem. This is achieved by reciprocally impacting and retracting broaches into the cancellous tissue (bone) with sufficient mechanical force to remove the bone. A series of rasps or broaches are employed to achieve this. These are conventionally applied using a rasp handle, to which the rasps are fitted and mechanically secured. Rasps are fitted and mechanically secured. Such instruments are reusable and must be sterilized between uses. Thus, a broach or rasp is a medical device that is used to prepare a bone to receive an implant. A broach or rasp handle is a medical device that can be used to hold the broach or rasp while a surgeon holds the broach or rasp handle. The broach or rasp handle has components that are used to engage and to disengage the broach or rasp. Rasp handles generally incorporate a mechanical linkage which secures and locks the rasp to the handle. The mechanism is often partially exposed from the body of the rasp handle, which enables ingress of blood, bone, and other particulates into the body of the handle. Such materials may adhere and dry in and on the mechanism before cleaning procedures begin, making subsequent cleaning and sterilization procedure difficult.

A femur rasp fastener is known in which a linkage is pivotally connected to a frame by way of a pivot shaft. The linkage includes a handle and a pivot head with a fulcrum arm that is pivotally connected to a suspension bar. The linkage is a single piece. No part of the linkage is separable from the pivot shaft in normal operation. This can make cleaning and sterilizing the femur rasp fastener difficult.

What is needed in the art is a broach handle having components which can be easily cleaned and/or sterilized.

SUMMARY OF THE INVENTION

The present invention provides a broach handle with a lever subassembly which is readily separable from the housing so that the lever subassembly and internal portions of the housing can be more easily cleaned and/or sterilized.

The invention in one form is directed to a medical instrument handle assembly for holding a medical instrument configured for preparing a bone to receive an implant. The medical instrument handle assembly includes: a housing including a housing pin; an elongate arm including a proximal end; a lever subassembly including a lever body and a lever latch, the lever body being pivotally connected to the proximal end of the elongate arm, the lever body and the lever latch being pivotally connected to one another and thereby being selectively positionable relative to one another between a first position and a second position, the first position being when the lever body and the lever latch are clamped about the housing pin, the second position being when the lever body and the lever latch are unclamped relative to the housing pin.

The invention in another form is directed to a method of using a broach handle assembly for holding a broach configured for preparing a bone to receive an implant. The method includes the steps of: providing a housing, an elongate arm, and a lever subassembly, the housing including a housing pin, the elongate arm including a proximal end, the lever subassembly including a lever body and a lever latch, the lever body being pivotally connected to the proximal end of the elongate arm, the lever body and the lever latch being pivotally connected to one another; pivoting the lever body and the lever latch relative to one another and thereby positioning, selectively, the lever body and the lever latch in a first position relative to one another, the first position being when the lever body and the lever latch are clamped about the housing pin; pivoting the lever body and the lever latch relative to one another and thereby positioning, selectively, the lever body and the lever latch in a second position relative to one another, the second position being when the lever body and the lever latch are unclamped relative to the housing pin.

An advantage of the present invention is that it provides a way for the handle subassembly to be readily released from the handle body.

Another advantage is that it provides a way to more easily, efficiently, and effectively clean the handle subassembly and the housing body.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention, and such exemplifications are not to be construed as limiting the scope of the invention in any manner.

DETAILED DESCRIPTION OF THE INVENTION

Figure 1:
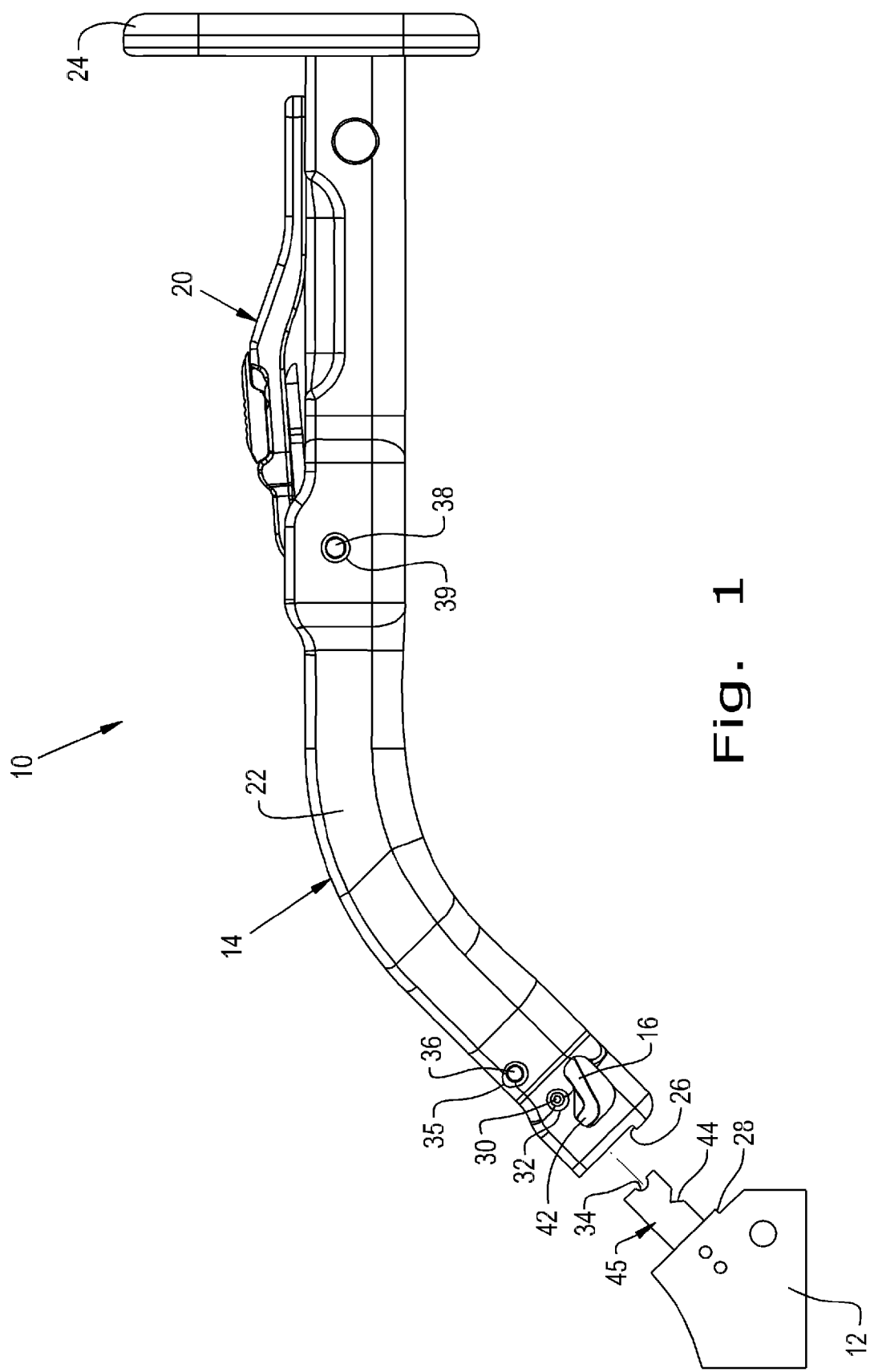
FIG. 1 is a side view of the broach handle assembly of the present invention.
Figure 2:
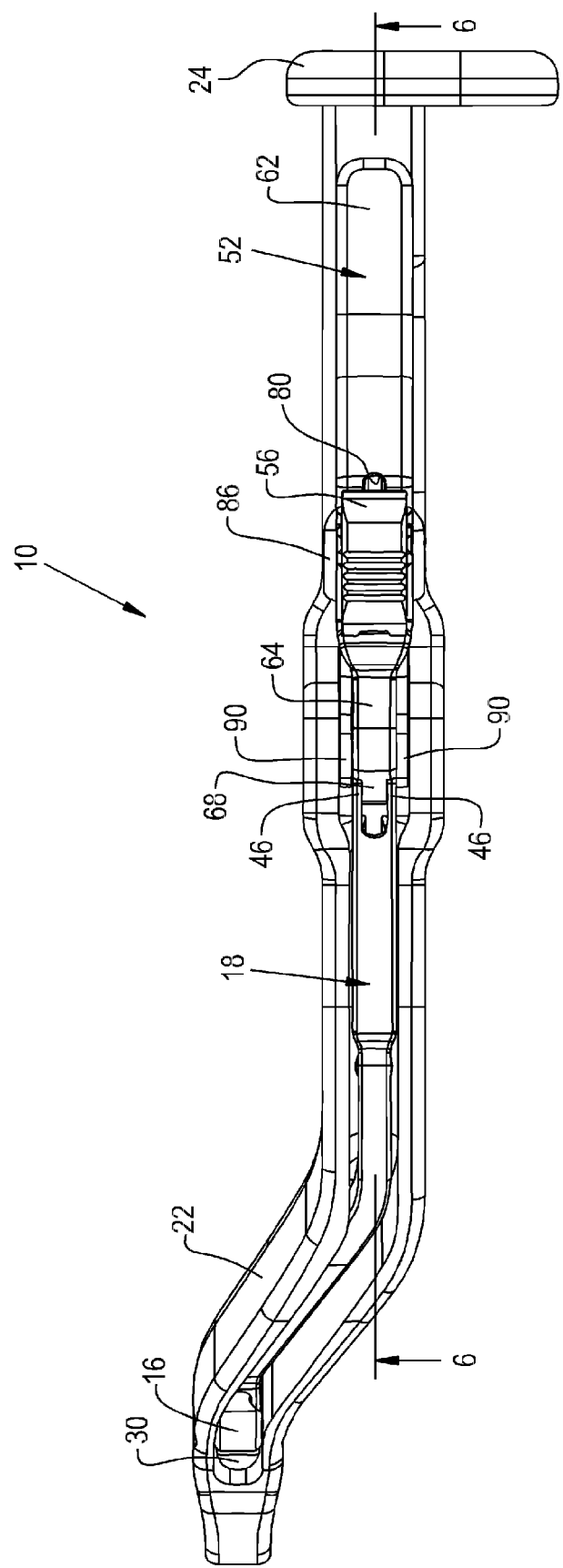
FIG. 2 is a top view of the broach handle assembly of FIG. 1.

Referring now to the drawings, and more particularly to FIGS. 1-7, there is shown a medical instrument handle assembly 10 (which can be a broach handle assembly or a rasp handle assembly for holding a medical instrument 12 (which can be a broach or a rasp) configured for preparing a bone (not shown) to receive an implant (not shown). Broach handle assembly 10 (which can also be referred to as a rasp handle assembly 10) generally includes a housing 14, a latch 16, an elongate arm 18, and a lever subassembly 20. The broach 12 (which can also be referred to as a rasp 12) can be used, for example, to prepare an intramedullary canal of a femur to receive an end of a femoral implant, the broach 12 preparing the intramedullary canal by, for example, sizing the intramedullary canal properly. FIG. 1 shows broach 12 schematically (and can be viewed as a test piece); an actual broach can be longer than what is shown and can have, for example, a cutting surface for preparing the bone.

Housing 14 includes a housing body 22. Housing body 22 can include a portion which generally has a U-shape in a transverse cross-section, the open portion of the U facing upwardly in FIG. 1 and being shown in FIG. 2. Because broach handle assembly 10 is double offset as shown in the drawings, housing body is offset both downwardly (shown in FIG. 1) and laterally (shown in FIG. 2). Housing body 22 can be offset laterally in either direction, depending upon design choice. While not shown in the drawings, housing body 22 can include a plurality of spaced apart holes (such as elliptically shaped holes, or any other shape) along the sides of housing body 22 and along the bottom (such as circular shaped holes, or any other shape) of housing body 22 (the closed portion of the U); these holes can provide a material savings and also make broach handle assembly 10 lighter in weight. Housing body 22 can be made of 17-4 PH stainless steel and can have a machine finish, housing body 22 being formed by machining, molding, or any other suitable method; this is provided by way of example and not by way of limitation. Housing 14 also includes an impaction plate 24 which is attached to a proximal end of housing body 22. Impaction plate 24 can be used to receive a blow, such as with a mallet. The force from the blow is transferred through broach handle assembly 10 to the broach 12, which is held by broach handle assembly 10 at the distal end of the broach handle assembly 10. Impaction plate 24 can be made of 17-4 PH stainless steel and can have a machine finish, impaction plate 24 being formed by machining, molding, or any other suitable method; this is provided by way of example and not by way of limitation. Housing body 22 can include a boss on the proximal end of housing body 22, the boss being a projection (this boss is not shown in the drawings). Impaction plate 24 can include a correspondingly shaped hole which receives this boss. Impaction plate 24 can be pushed onto this boss. TIG (tungsten inert gas) welds can be placed around the hole in impaction plate 24 on the proximal face of impaction plate, and this weld/join area can be dressed flush. A TIG weld can also be placed around the join of the boss to impaction plate 24 (on the distal face of impaction plate 24), and this weld/join area can be dressed to have a predetermined radius of curvature. The distal end face of housing body 22 can include a ledge 26 which matingly corresponds to a ledge 28 on broach 12. Further, the distal end of housing body 22 can include a crossbar 30 which extends transversely from one leg of the U of housing body 22 to the other leg and is inserted into holes 32 of each of the legs. Crossbar 30 is also referred to as a pin 30. Pin 30, for example, can have a diameter of 3.2 mm and a length of 12.7 mm; this is provided by way of example and not by way of limitation. Crossbar 30 can serve as a brace which seats in a recess 34 in broach 12, thereby providing additional support for broach 12 when engaged with broach handle assembly 10.

The distal end of broach handle assembly 10 can be designed various ways depending upon design choice. For instance, the distal end face of housing body 22 can be substantially flat (rather than having ledge 26). Also, housing can also include a spigot (not shown) which is a projection on the distal end face of housing body 22, spigot projecting outside of and away from the distal end face of housing body 22. Spigot can be made of 17-4 PH stainless steel and have a machine finish; this is provided by way of example and not by way of limitation. Spigot can be press fit into a hole in the distal end of housing body 22. TIG welds can be placed outside of housing body 22 and on the inside of housing body 22 to join spigot to housing body 22, and the holes can be filled between spigot and housing body 22, this weld/join area being dressed flush on both sides. Spigot can be used to seat within a corresponding recess in the broach so as to provide a more stable connection between broach handle assembly and the broach and/or to properly position the broach relative to broach handle assembly. Spigot can be formed by machining, molding, or any other suitable method.

Housing body 22, impaction plate 24, and (optionally) spigot can be heat treated (for example, H900 RC41-44) and passivated, and a satin finish can be provided. This is provided by way of example and not by way of limitation.

Housing 14 also includes a first housing pin 36 and a second housing pin 38. First housing pin 36 extends transversely through housing body 22 through each leg of the U of housing body 22, first housing pin 36 being positioned at the distal end of housing body 22. First housing pin 36 also extends through latch 16 and thereby pivotally couples latch 16 with housing body 22, as latch 16 can pivot on first housing pin 36. In one embodiment, first housing pin 36 can be made of any suitable material (such as stainless steel) and can have a diameter of 4 mm and a length of 15 mm; this is provided by way of example and not by way of limitation. Second housing pin 38 also extends transversely through housing body 22 through each leg of the U of housing body 22, second housing pin 38 being positioned in generally a middle position of housing body 22. Lever subassembly 20 can clamp around second housing pin 38 and thereby pivot on second housing pin 38. As should be appreciated, the second housing pin 38 can define a pin axis that the lever subassembly 20 rotates about to clamp the second housing pin 38. The second housing pin 38 can also be rigid to allow the lever subassembly 20 to stably clamp the second housing pin 38. As used herein, the second housing pin 38 being "rigid" refers to the second housing pin 38 being formed of a rigid material and/or being rigidly supported by the housing 14 to allow the lever subassembly 20 to stably clamp about the second housing pin 38. In one embodiment, second housing pin 38 can be made of a rigid metal such as stainless steel and can have a diameter of 5 mm and a length of 24 mm; this is provided by way of example and not by way of limitation.

Figure 3:
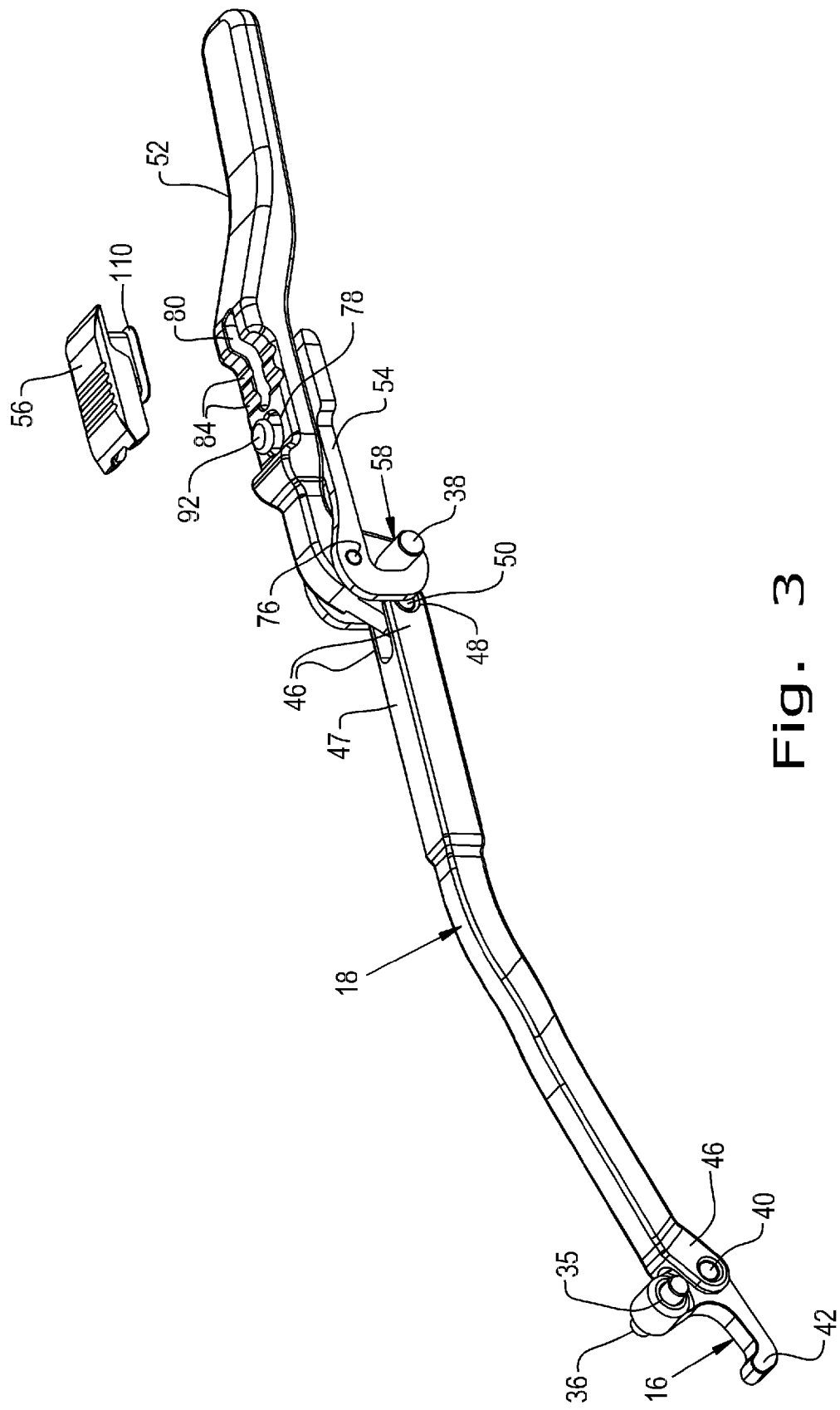
FIG. 3 is an exploded, perspective view of the broach handle assembly of FIG. 1, with portions broken away.

As shown in FIG. 3, latch 16 generally has a V-shape which thus has two legs. Near the free end of one leg is a through-hole which receives first housing pin 36. Latch 16 pivots on first housing pin 36, and latch 16 is thereby pivotally coupled with housing body 22. At the corner of the V of latch 16, latch 16 has another through-hole which receives another pin 40. This pin 40 pivotally couples latch 16 with a distal end of elongate arm 18. At the free end of the other leg of the V of latch 16 is a projection 42 which serves as a locking mechanism to lock latch 16 to the broach 12. When latch 16 is rotated in the clockwise direction on a longitudinal axis through first housing pin 36 (viewed as shown in FIG. 1), then latch 16 moves to a locking position so as to seat within a corresponding recess 44 on broach 12. When latch 16 is rotated in a counterclockwise direction on a longitudinal axis through first housing pin 36 (viewed as shown in FIG. 1), then latch 16 moves to an unlocking position so that latch is released from broach 12. Latch 16 can be made of 17-4 PH stainless steel, be heat-treated at Rc41-44, have a fine bead finish, and be passivated; this is provide by way of example and not by way of limitation. Latch 16 can be formed by machining, molding, or any other suitable method.

Elongate arm 18 extends between latch 16 and lever subassembly 20 and thus couples latch 16 and lever subassembly 20 together. Elongate arm 18 (which can also be referred to as a spring) follows the offset shape of housing body 22 and thus also projects downwardly and laterally. Elongate arm 18 can be made of 420 stainless steel, be heat-treated at HRc 48-52, and have a satin finish; this is provided by way of example and not by way of limitation. Elongate arm 18 includes a distal end and a proximal end 47 (the distal end being towards broach 12 and the proximal end 47 being toward impaction plate 24). Each of the distal end and the proximal end 47 of elongate arm 18 includes a forked section 46. The forked section 46 of the distal end of elongate arm 18 includes two legs which straddle the sides of latch 16, each leg of the forked section 46 including a through-hole which aligns with the corner through-hole of latch 16, pin 40 extending through each of these leg through-holes and also the corner through-hole of latch 16 so that latch 16 is pivotally coupled with elongate arm 18. In this way, the distal end of elongate arm 18 is moveably coupled with housing 14. Similarly, the forked section 46 of the proximal end 47 of elongate arm 18 also includes two legs which straddle the sides of lever body 52, each leg of forked section 46 of proximal end 47 of elongate arm 18 including a through-hole 48 which aligns with a through-hole 72 of lever body 52, pin 50 extending through each of these leg through-holes 48 and also through-hole 72 of lever body 52 so that elongate arm 18 is pivotally coupled with lever body 52. Thus, lever body 52 is pivotally connected to the proximal end 47 of elongate arm 18. Forming the forked section 46 of the proximal end 47 of elongate arm 18 can include a break edge all around. As lever subassembly 20 is rotated, elongate arm 18 is moved distally or proximally so as to rotate latch 16 clockwise or counter-clockwise and thereby either lock broach 12 to, or unlock broach 12, from broach handle assembly 10.

Lever subassembly 20 includes a lever body 52, a lever latch 54, and a lever button 56. Lever body 52 and lever latch 54 are pivotally connected to one another and thereby are selectively positionable relative to one another between a first position 58 (see FIGS. 1-3 and 6) and a second position 60 (see FIG. 5), the first position 58 being when lever body 52 and lever latch 54 are clamped about second housing pin 38, the second position 60 being when lever body 52 and lever latch 54 are unclamped relative to second housing pin 38 (whether or not second housing pin 38 is in second slot 70).

Lever body 52 is a generally elongate structure with a distal end which projects downwardly. Lever body 52 includes a lever body handle 62 at the proximal end of lever body 52. Lever body handle 62 can be used by a surgeon to rotate lever body clockwise or counter-clockwise in FIG. 1 and to lift lever body 52 out of the interior of the U of handle body 22 (for example, so that various parts of broach handle assembly 10 can be cleaned and/or sterilized). Lever body 52 includes a fork 64 at the distal end of lever body 52. Fork 64 has a first projection 66 and a second projection 68 which together form a first slot 70 therebetween which receives second housing pin 38. Second projection 68 of fork 64 has a reduced thickness relative to first projection 66 and is pivotally connected with proximal end 47 of elongate arm 18 by way of a through-hole 72 through second projection 68 and pin 50 extending through this through-hole 72 and elongate arm 18. Further, fork 64 includes another through-hole 74 which receives a pin 76 which pivotally connects lever body 52 and lever latch 54 together. Lever body further includes a middle section positioned between lever body handle 62 and fork 64. This middle section includes two higher portions and a saddle positioned therebetween, as shown in FIGS. 1 and 3-6. In this middle section of lever body 52, lever body 52 further includes a hole 78 and a second slot 80, both of which run generally parallel to one another. Hole 78 is generally circular in cross-section (but can have an elongation along the longitudinal axis of lever body) and is positioned closer to fork 64 than second slot 80. Second slot 80 is generally elliptical in cross-section and thus has a longitudinal extent. Second slot 80 can have a break edge at the top and a flared portion 82 at the bottom. The dimensions of second slot 80 can be checked using a predetermined size of a ball gauge (for example, S ϕ (diameter) 6 mm or S ϕ ¼ inch ball gauge). In this middle section of lever body 52, lever body 52 also includes grooves 84 extending transversely relative to lever body 52, grooves 84 extending on both sides of second slot 80. FIG. 3 shows that lever body 52 includes two such grooves 84 (or, four such grooves 84 if each groove 84 on each side of second slot 80 is considered a single groove 84). Lever body 52 can be made of 17-4 PH stainless steel, can be heat-treated at COND H 900, have a fine bead finish, and be passivated; this is provided by way of example and not by way of limitation.

Figure 4:
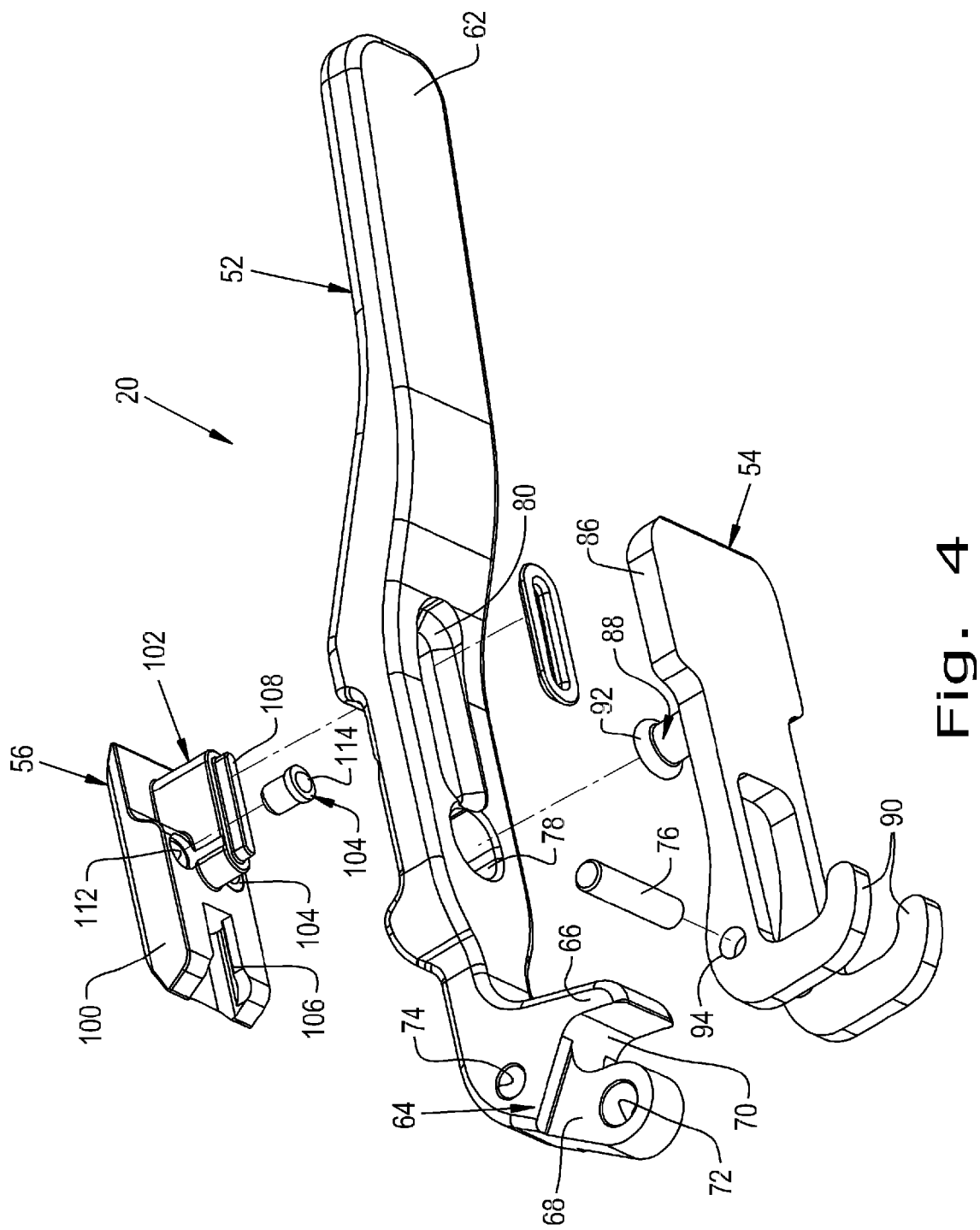
FIG. 4 is an exploded, perspective view of the lever subassembly of FIG. 1.
Figure 5:
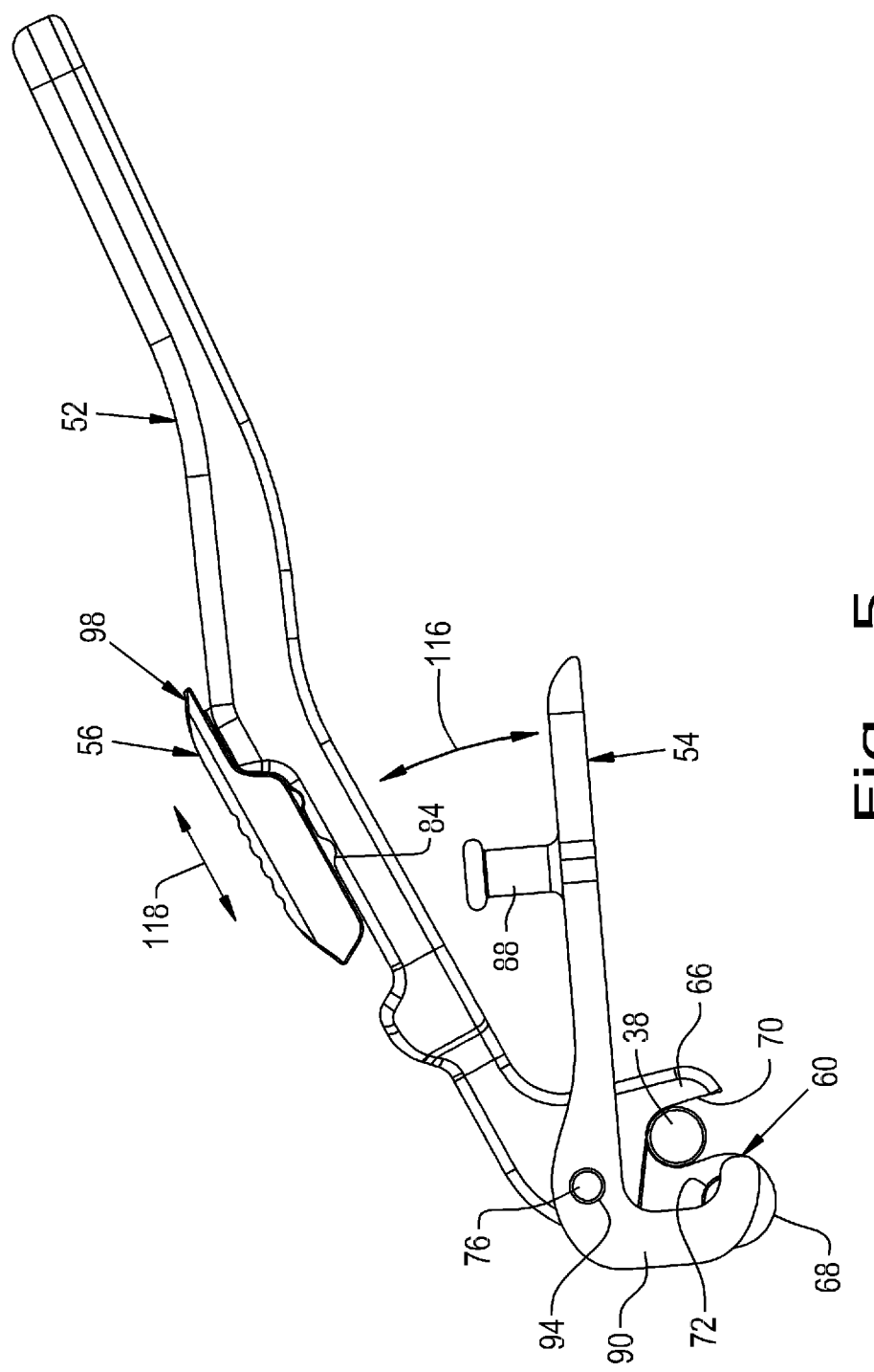
FIG. 5 is a side view of the lever subassembly of FIG. 1.
Figure 6:
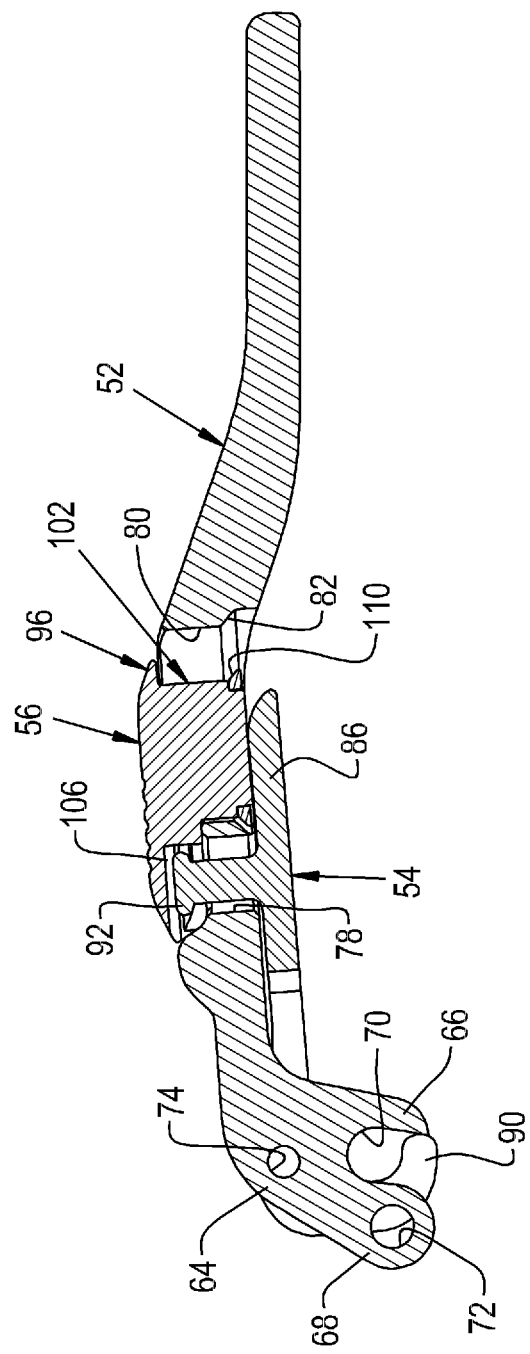
FIG. 6 is a cross-sectional view of the lever subassembly taken along line 6-6 in FIG. 2.
Figure 7:
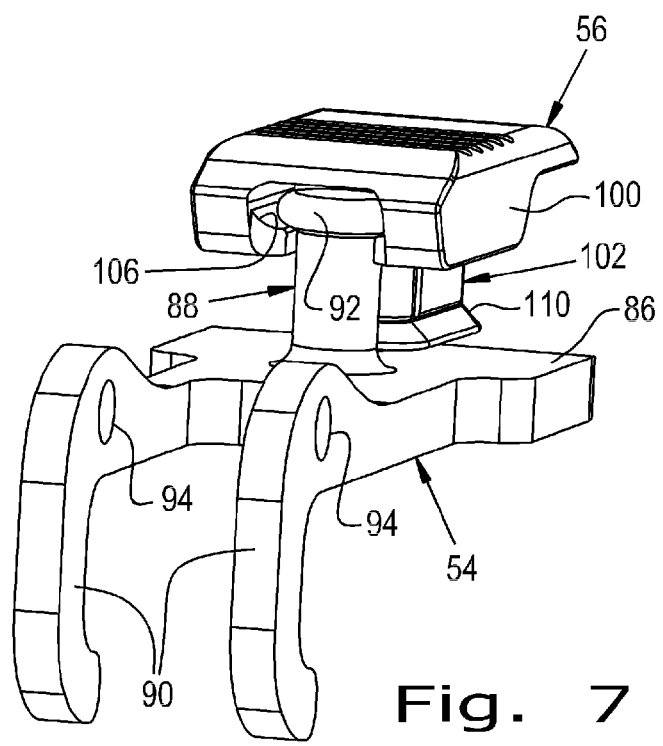
FIG. 7 is a perspective view of the lever subassembly of FIG. 1, with portions broken away.

Lever latch 54 includes a platform 86, a boss 88, a first hook 90, and a second hook 90. Platform 86, as shown in FIGS. 4 and 7, can be a generally planar structure. Boss 88 is an upstanding structure which is mounted on platform 86 and extends generally perpendicularly to platform 86. Boss 88 can include a cylindrical tower and a head 92 mounted on top of the cylindrical tower. Head 90 has a width which is wider than the diameter of the cylindrical tower. First and second hooks 90 extend from platform 86 and run parallel relative to one another. Each hook 90 extends to the lateral sides of fork 64 and to the outside of the proximal end 47 of elongate arm 18. Each hook 90 includes a generally U-shaped section like a hook; the U-shaped section of each hook 90 receives second housing pin 38 inside the U of each hook 90. Each hook 90 includes a through-hole 94 which receives pin 76 so that lever latch 54 and lever body 52 are pivotally connected to one another. Pin 76 can, for example, have a diameter of 3 mm and a length of 12.5 mm; this is provided by way of example and not by way of limitation. Fork 64 of lever body 52 is positioned between first hook 90 and second hook 90. First hook 90 and second hook 90 cooperate with fork 64, and first hook 90, second hook 90, and lever body 52 thereby clamp second housing pin 38 when lever body 52 and lever latch 54 are in first position 58. Boss 88 extends through hole 78 when lever body 52 and lever latch 54 are in first position 58. Boss 88 is at least partially retracted through hole 78 when lever body 52 and lever latch 54 are in second position 60. Lever latch 54 can be made of 17-4 PH stainless steel, can be heat-treated at COND H 900, have a fine bead finish, and be passivated; this is provided by way of example and not by way of limitation.

Lever button 56 is slidably attached to lever body 52. Lever button 56 is selectively positionable between a first lever button position 96 (see FIGS. 1-2 and 6-7) and a second lever button position 98 (see FIG. 5). First lever button 96 position is when lever button 56 is attached to boss 88. Second lever button position 98 is when lever button 56 is detached from boss 88. Lever button 56 includes a lever button body 100, a downwardly depending projection 102, and two plungers 104. Lever button body 100 includes a top surface with substantially parallel ridges and/or grooves extending transversely across the top surface of lever button body 100, as shown in the figures, such as FIG. 3; these ridges and/or grooves provide a gripping surface for a thumb or finger of a surgeon to manipulate lever button 56 by sliding lever button 56 forward or backward along lever body 52. Lever button body 100 further includes a raceway 106 positioned under the top surface of lever button body 56. Raceway 106 is open to the distal end of lever button body 100 and extends longitudinally through a portion of lever button body 100. Raceway 106 has a substantially T-shaped cross-section, as shown in FIGS. 4 and 7. Raceway 106 is configured for slidably receiving head 92, lever button 56 being in first lever button position 96 when head is attached to raceway 106 and, more specifically, when plungers 104 are seated in the forward-most (distal) grooves 84. Projection 102 depends downwardly from lever button body 100 and generally has an elliptical cross-section. Projection 102 has a further smaller projection 108 (which can be referred to as a boss 108) projecting from the bottom of projection 102. Projection 102 includes a locking cap 110 (which can be referred to as a locking skirt) attached to boss 108, locking cap 110 flaring outwardly moving downwardly. Projection 102 slides within slot 80 of lever body handle 62, the length of slot 80 being greater than the length of projection 102, the width of slot 80 accommodating the width of projection 102 so that projection 102 can slide within slot 80. The flared bottom of locking cap 110 is wider than the width of the main portion (the portion immediately above flared portion 82) of slot 80; thus, locking cap 110 prevents projection 102 from being pulled through slot 80 and thus locks projection in slot 80. The flared shape of locking cap 110 can matingly correspond to the flared portion 82 of second slot 80 in lever body 52. Thus, lever button 56 includes a single downwardly depending projection 102 extending through second slot 80, downwardly depending projection 102 being configured for being moved in second slot 80 when lever button 56 is moved between first lever button position 96 and second lever button position 98. Lever button body 100 further includes two substantially identical blind holes 112 positioned on each side of projection 102, blind holes 112 opening downwardly. Blind holes 112 are shown in FIG. 4 (only one blind hole 112 is labeled in FIG. 4, the other blind hole 112 having already received therein a plunger 104, both blind holes 112 being substantially identical to one another). Each blind hole 112 receives a plunger 104 therein (each plunger 104 being substantially identical to one another), the respective plunger 104 being attached to blind hole 112 by a press fit. For illustrative purposes, plungers 104 are omitted from FIG. 7. Each plunger 104 includes a ball 114 (shown in FIG. 4) which is biased outwardly by a spring inside the housing of plunger 104; the balls 114 of each plunger 104 seat in a respective groove 84 to lock lever button 56 in one of two positions (corresponding to first lever button position 96 and second lever button position 98), the balls 114 being depressed inwardly as balls 114 travel over the raised portions between the grooves 84. Each of the parallel grooves 84 corresponds to first and second lever button positions. In other words, when lever button 56 is in the first lever button position 96, plungers 104 (more specifically, the respective balls 114) are seated in the distal grooves 84; on the other hand, when lever button 56 is in the second lever button position 98, plungers 104 are seated in the proximal grooves 84. Thus, plungers 84 travel over lever button 52 to be either in a closed or an open position as plungers 104 interfere with grooves 84. Two plungers 104 are used to obtain better stability. By way of example and not by way of limitation, each plunger 104 can be a Wixroyd 32300.W0003 spring ball plunger made of stainless steel, DELRIN®, or brass and having a housing diameter of three millimeters and a housing length of four millimeters; this is provided by way of example and not by way of limitation. Lever button body 100, downwardly depending projection 102, and locking cap 110 can be made of 17-4 PH stainless steel, can be heat-treated at COND H900, have a satin finish, and be passivated; this is provided by way of example and not by way of limitation.

The broach handle assembly 10 can be assembled as described below. This assembly process is provided by way of example and not by way of limitation. Lever subassembly 20 can be assembled prior to attaching lever subassembly 20 to elongate arm 18 or housing 14. Plungers 112 can be pressed into blind holes 112 in lever button 56. Lever button 56 can then be placed into second slot 80 in lever body 52. Locking cap 110 can then be pressed onto boss 108 of downwardly depending projection 102. Locking cap 110 can then be laser welded to lever button 56; this weld/join area can be dressed and wipe passivated. Further, holes 94 of lever latch 54 should be aligned with holes 74 in lever body 52. Pin 76 can then be inserted through each of these holes 74, 94 to make the connection between lever latch 54 and lever body 52; pin 76 can be press-fitted to lever latch 54. This pin 76 can be laser welded to lever latch 54 on both exterior sides of lever latch 54, pin 76 thereby being sealed; this weld/join area can be dressed and wipe passivated (alternatively, this pin 76 can be laser welded to lever body 52 on both exterior sides, and this weld/join area can be dressed (flush, for example) and wipe passivated). The functions of lever subassembly 20 can then be checked. Lever button 56 stops in grooves 84 of lever body 52. Lever latch 54 swings freely relative to lever body 52. Lever latch 54 can be locked into lever button 52 (for example, using boss 88 and raceway 106, as well as plungers 104 and grooves 84).

After assembly of lever subassembly 20, the remainder of broach handle assembly 10 can be assembled. The hole in the corner of the V of latch 16 is aligned with the holes in the distal end fork 46 of elongate arm 18, and pin 40 is pressed through each of these holes. This pin 40 can have a diameter of 4 mm and a length of 8 mm; this is provided by way of example and not by way of limitation. The top of this pin 40, on both sides (that is, the exterior of fork 46 of the distal end of elongate arm 18), can be laser welded to the distal end fork 46 of elongate arm 18 so that pin 40 is welded to elongate arm 18 and latch 16 can pivot on pin 40; this weld/join area can be dressed flush and then wipe passivated (alternatively, this pin 40 can be laser welded to latch 16 on both exterior sides of latch 16, and this weld/join area can be dressed flush and wipe passivated). Further, hole 72 in lever body 52 is aligned with holes 48 in fork 46 of the proximal end of elongate arm 18, and pin 50 is pressed through each of these holes 48, 72. This pin 50 can have a diameter of 4 mm and a length of 8 mm; this is provided by way of example and not by way of limitation. The top of this pin 50, on both sides (that is, the exterior of fork 46 of the proximal end 47 of elongate arm 18), can be laser welded to fork 46 of the proximal end 47 of elongate arm 18 so that pin 50 is welded to elongate arm 18 and lever body 52 can pivot on pin 50; this weld/join area can be dressed flush and then wipe passivated (alternatively, this pin 50 can be laser welded to lever body 52 on both exterior sides of lever body 52, and this weld/join area can be dressed flush and wipe passivated). Latch 16, elongate arm 18, and lever subassembly 20 are checked to make sure that they move freely relative to one another. First, the hole in the free end of a leg of the V of latch 16 and holes 35 in the distal end of housing body 22 are aligned, and first housing pin 36 is pushed into holes 35 as well as into the hole in the free end of the leg of the V of latch 16. A TIG weld can be used to weld first housing pin 36 to both sides of housing body 22 (such as on the exterior sides of housing body 22) so that first housing pin 36 is welded to housing body 22 and latch 16 can rotate on first housing pin 36; this weld/join area can be dressed flush and wipe passivated. Thus, latch 16 can be mounted to housing body 22 after latch 16 is joined to elongate arm 18, or, alternatively, latch 16 can be mounted to housing body 22 before latch is joined to elongate arm 18. If the latter order is used, pin 40 used to join latch 16 and the distal end of elongate arm 18 can be inserted through the corresponding holes of latch 16 and elongate arm 18 when latch 16 is rotated so that the corner hole of latch 16 is above the U of housing body 22 or when latch 16 is rotated so that the corner hole of latch 16 is within the interior of the U of housing body 22. If the latter latch position is used, then optionally holes (not shown) in each leg of the U of housing body can be formed in the distal end of housing body 20 generally below holes 35 and these holes can be used; that is, the corner hole in latch 16, the distal end holes in fork 46 of the distal end of elongate arm 18, and the aforesaid housing holes of housing body 22 can be aligned with one another and the V-corner pin 40 can be inserted through each of these aforesaid housing holes (but pin 40 would not remain in these housing holes, so that latch 16 could rotate within housing body 22) (the pin 40 could also be removed through one of these aforesaid housing holes, if necessary). Further, second housing pin 38 is pushed into holes 39 in housing body 22. A TIG weld can be used to weld second housing pin 38 to both sides of housing body 22 at holes 39 (such as on the exterior sides of housing body 22) so that second housing pin 38 is welded to housing body 22; this weld/join area can be dressed flush and wipe passivated. Further, crossbar 30 can be pressed into holes 32 in housing body, and crossbar 30 can be welded to housing body 12; this weld can be accomplished by a laser weld or a TIG weld (after welding, this weld/join area can be dressed flush and wipe passivated). Lever subassembly 20 is attached (clamped) to second housing pin 38. Lever button 56 is pulled back so that lever button 56 and lever latch 54 can be moved to second position 60. Lever body 52 and lever latch 54 are pivoted relative to one another so that lever body 52 and lever latch 54 are in the second position 60 and thus open (unclamped) relative to one another. Second housing pin 38 is then inserted into slot 70 formed by lever body 52 (that is, lever body 52 is mounted onto second housing pin 38 by way of slot 70). Lever body 52 is then rotated towards housing body 22 (in a clockwise direction, as shown by double-arrow 116 in FIG. 5) so that lever body 52 and lever latch 54 are moved to first position 66 and thus closed and thereby clamped around second housing pin 38. Lever button 56 can then be moved forward (as shown by double-arrow 118 in FIG. 5) to lock lever button 56 and lever latch 54 in the clamped position. The following are checked: that all pinned joints move freely; that lever subassembly 20 latches onto second housing pin 38; that broach handle assembly 10 holds securely a male test piece or broach 12 (it is noted that broach handle assembly 10 can be designed so that it holds a female test piece instead of a male test piece); that broach handle assembly 10 releases the test piece or broach 12; and that lever subassembly 20 detaches from second housing pin 38.

It is noted that each of the pins used in the broach handle assembly of the present invention can be made of stainless steel or any other suitable material. Further, each of the pin holes in housing body 22 is on both legs of the U of housing body 22. Any of the pins disclosed herein could be longer or shorter than what is described herein. Any of the pins attached to housing body 22 herein can be dressed flush and then wipe passivated after welding. Further, unless otherwise provided herein, any of the parts of the broach handle assembly of the present invention can be made by machining, molding, stamping, pressing, or any other suitable method. Further any of the finishes (such as fine bead finish, which can be a form of a blast finish) can be other than what has been described herein and thus be, for example, a satin finish. Further, the material of any of the components of broach handle assembly 10 can be other than what has been described herein and thus be, for example, Nitronic® 60 stainless steel. Further, latch 16 and/or lever latch can be made of 455C stainless steel for example. Further, elongate arm 18 can be made square to the first joint, and then a transition can be done to latch 16. Further, the chamfer on housing 14 and/or housing body 22 can be reduced as needed for purposes of welding.

In use, it is presumed that lever subassembly 20 is initially not connected to second housing pin 38. Thus, lever button 56 is pulled back (see double-arrow 118) to second lever button position 98 so that plungers 104 seat in the rear-most groove 84 and head 92 is clear of raceway 106 of lever button 56. Lever subassembly 20 is opened by pivoting lever body 52 and lever latch 54 to the open position (see double-arrow 116) to fully open slot 70 (and thus to second position 60 relative to one another). In performing this pivoting action, at least one of lever body 52 and lever latch 54 is moved away from the other. Slot 70 is then mounted to second housing pin 38 by inserting second housing pin 38 into slot 70. Lever subassembly 20 is then closed about (and thus clamped to) second housing pin 38 by pivoting at least one of lever body 52 and lever latch 54 towards the other (see double-arrow 116), lever body 52 and lever latch 54 then being in the first position 58 relative to one another. After bringing lever body 52 and lever latch 54 together, head 92 projects through hole 78. Lever button 56 is then slid forward (se double-arrow 118) to first lever button position 96 until plungers 104 seat in the forward-most groove 84, head 92 then being locked to raceway 106. Lever subassembly 20 can then be pivoted about second housing pin 38 in either direction. To attach a broach 12 to broach handle assembly 10, lever subassembly 20 is rotated in a counter-clockwise direction (see doubled-arrow 116). In this way, latch 16 is caused to rotate in a counter-clockwise direction (as viewed in FIG. 1) to a disengagement position (a pulled-back position). The protrusion 45 of broach 12 is then inserted into the distal end opening of housing body 22. Alignment features in the distal face of housing body 22 can be mated with corresponding alignment features on broach 12 (such as ledges 26, 28). Further crossbar 30 can seat in recess 34. Lever subassembly 20 (lever body 52 and lever latch 54 still being in a clamped position about second housing pin 38) is then rotated (see double-arrow 116) in a clockwise direction (in FIG. 5). This rotation causes latch 16 to rotate in a clockwise direction. In this way, the locking projection 42 on one leg of latch 16 is moved to an engagement position relative to broach so that the locking projection 42 of latch seats in a corresponding recess 44 in projection 45 of broach 12, broach 12 then being locked to broach handle assembly 10. Broach 12 can then be used to prepare a bone for an implant. Broach 12 can be released from broach handle assembly 10 by rotating lever subassembly 20 (lever body 52 and lever latch 54 still being in a clamped position about second housing pin 38) in a counter-clockwise direction (see double-arrow 116 in FIG. 5). This rotation causes latch 16 to rotate in a counter-clockwise direction. In this way, the locking projection 42 of latch 16 is moved to the disengagement position relative to broach 12 so that the locking projection 42 of clamp 16 unseats from the corresponding recess 44 in projection 45 of broach 12, broach 12 then being unlocked from broach handle assembly 10. Projection 45 of broach 12 can then be removed from the hole in the distal face of housing body 22. Further, lever subassembly 20 can be unclamped from second housing pin 38 and lifted out of the U of housing body 22. In this way, lever subassembly 20, as well as other components of broach handle assembly 10, can be cleaned and/or sterilized in an easier and more efficient and effective manner. Lever subassembly 20 can be unclamped from second housing pin 38 by moving lever button 56 back to the rear-most groove 84 (to second lever button 56 position), pivoting lever body 52 and lever latch 54 away from each other (to second position 60—the unclamped position), and lifting lever body 52 so that second housing pin 38 is removed from slot 70. Further, the lever subassembly 20 can function similarly regardless of whether the broach 12 is a male broach or a female broach. Lever subassembly 20, for either a male or female broach, is that the lever subassembly 20 selectively pushes and pulls back the elongate arm 18 as necessary.

Thus, during use, after unclamping lever subassembly 20 from second housing pin 38 (such that a path is cleared so that second housing pin 38 can be removed from first slot 70), second housing pin 38 can be removed from first slot 70, and lever subassembly 20 can be lifted out the open portion of the U of housing body 22. In so doing, lever subassembly 20 and elongate arm 18 can be lifted out of housing body 22 by way of the open portion of the U of housing body 22. Because lever subassembly 20 is still attached to elongate arm 18, elongate arm 18 is still attached to latch 16, and latch 16 is still attached to housing body 22 by way of first housing pin 36, lever subassembly 20 and elongate arm 18 can be lifted out of and away from housing body 22 by pivoting lever subassembly 20, elongate arm 18, and latch 16 together in a counter-clockwise direction (as viewed in FIG. 1) about first housing pin 36. In this way, lever subassembly 20 and elongate arm 18 can be exposed out of housing body 22 and cleaned and/or sterilized in an easier manner, lever subassembly 20, elongate arm 18, and latch 16 still, however, being attached to housing body 22 by way of first housing pin 36. By remaining attached to housing body 22 by way of first housing pin 36, the parts of lever subassembly 20, elongate arm 18, and latch 16, and their various connecting pins (40, 50, 76) are less likely to be lost during the cleaning/sterilization operation.

Figure 8:
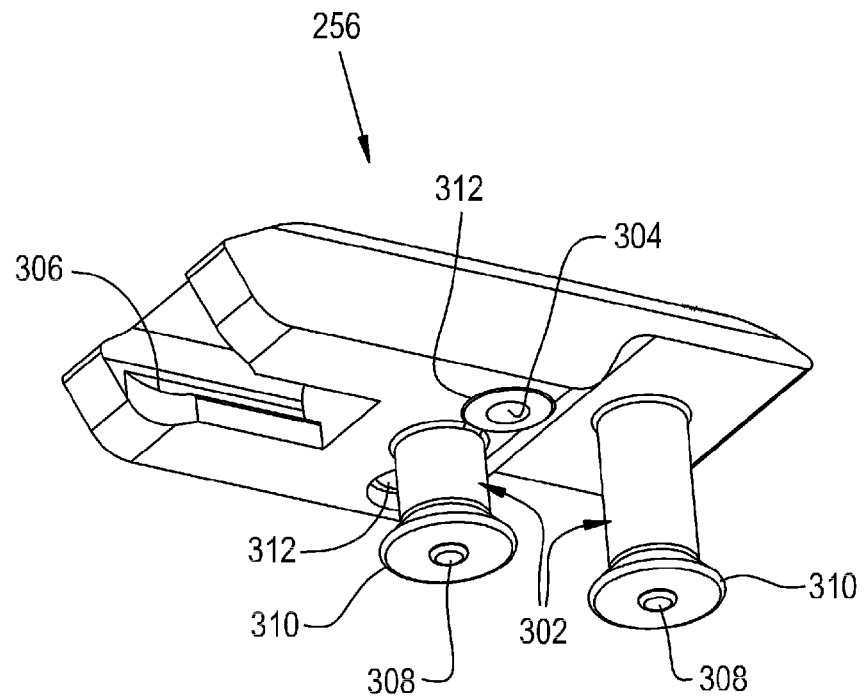
FIG. 8 is a perspective view of another embodiment of the lever button according to the present invention.

FIG. 8 shows an alternative embodiment of the lever button according to the present invention. Lever button 256 is similar to lever button 56. Corresponding parts regarding the lever button of the present invention are raised by 200 in FIG. 8 relative to what is shown in FIGS. 1-7. Lever button 256 includes raceway 306 and blind holes 312 for receiving plungers 304. Lever button 256 has two plungers 304 but only one plunger 304 is shown in FIG. 8, for illustrative purposes. However, rather than having a single downwardly depending projection, lever button 256 in FIG. 8 has two downwardly depending projections 302. Each projection 302 depends downwardly to the same level. Projections 302 slide within second slot 80 and function similarly relative to single projection 102. Projections 302 each include locking caps 310 which function similarly to locking cap 110. Each locking cap 310 can be mounted to a boss 308 like that described above relative to locking cap 110 and in a substantially similar way as described above. Projections 302 are configured for being moved in second slot 80 when lever button 256 is moved between first lever button position 96 and second lever button position 98. Lever button 256 is assembled to lever body 52 and functions in substantially similar ways as lever button 56 described above.

In summary, the double offset rasp handle with cleanable linkage of the present invention (which is referred to herein as broach handle assembly 10, which can be generally referred to as a handle assembly) is intended for use as an instrument in Total Hip Replacement (THR). During the surgery to implant a hip replacement prosthesis, it is accepted practice to excavate the cancellous tissue from the proximal section of the femur, in order to insert a femoral prosthesis. This excavation is performed using rasps or broaches. The rasps or broaches are secured in an instrument commonly described as a broach handle or rasp handle. The present invention thus applies to both broach handles and rasp handles, and for simplicity a reference to one (a broach handle or a rasp handle) refers just as well to the other (similarly, a reference to broach herein refers just as well to a rasp). A mechanical linkage integral to the device (the handle assembly) retains and secures the broach to the handle assembly, while allowing the broach to be detached from the handle quickly if necessary (a "quick release" mechanism).

As the handle assembly (rasp handle assembly, broach handle assembly) and broaches (as well as rasps) are reusable surgical instruments, and in order to avoid infection to either patient or other parties involved in the surgery, it is imperative that such instruments be sterilized between uses. It is also important that any mechanical parts within the device (the handle assembly) can be sufficiently irrigated by cleaning media to completely remove surgical residues and thereby produce sterility.

The double offset rasp handle (which is referred to herein as the handle assembly) includes a linkage which is normally contained within the body of the device but which can be mechanically released from the body to expose it more freely but which is not detachable from the body. This facility reduces the probability of losing a component part, and most significantly presents distinct advantages for direct inspection, cleaning, and sterilization of the device component parts. The double offset rasp handle has been developed for surgery involving the anterior approach to the hip, and the overall geometry of the device (the handle assembly) is designed for that purpose. However, the linkage (the linkage can be understood to be the elongate arm of the present invention), including the release mechanism (the release mechanism can be understood to be the lever subassembly of the present invention), can be applied to rasp handles intended for other approaches to the hip. This includes lateral and posterior approaches, where the overall geometry of the device is curved or straight. That is, lever subassembly of the present invention can be used for various approaches (for example, anterior, lateral, posterior) and can be used with not only double offset handles but also with curved or straight handles.

Further, the handle assembly of the present invention (for example, the double offset rasp handle or double offset broach handle) with the cleanable linkage includes a mechanism which greatly improves the ease of cleaning and sterilization of the handle assembly. It achieves this through an integral mechanism which can be employed to pivot the components of the mechanism from the handle body without completely detaching the linkage from the main body of the device. This is shown and described herein. While this device is disclosed as being a double offset rasp/broach handle assembly, the device of the present invention could equally be applied in similar rasp or broach handle assemblies of straight or curved geometry.

The present invention advantageously provides a handle assembly in which the broach/rasp locking mechanism can be exposed from the body (the handle body), thereby enabling improved cleaning and ease of sterilization. This is achieved without detaching the linkage from the body (the handle body). In other words, lever subassembly 20 is releasable from the second housing pin 38 of housing 14 but is still attached to housing body 22 by way of elongate arm 18, latch 16, and first housing pin 36. The mechanism is specifically contoured to suit a double offset rasp handle. However, the geometry of the linkage and mechanism can be adapted to suit curved or straight rasp handles.

By exposing the linkage (the elongate arm) for cleaning, the linkage may be mishandled, bent, or abused by staff involved in the cleaning process. However, the handle assembly of the present invention is considered advantageous to both the clinical staff, cleaning and sterilization process staff, and to the patient in terms of improved cleaning and ease of sterilization.

The present invention further provides a method of using a medical instrument handle assembly 10 for holding a medical instrument 12 configured for preparing a bone to receive an implant. The method includes the steps of: providing a housing 14, an elongate arm 18, and a lever subassembly 20, housing 14 including a housing pin 38, elongate arm 18 including a proximal end 47, lever subassembly including a lever body 52 and a lever latch 54, lever body 52 being pivotally connected to proximal end 47 of elongate arm 18, lever body 52 and lever latch 54 being pivotally connected to one another; pivoting lever body 52 and lever latch 54 relative to one another and thereby positioning, selectively, lever body 52 and lever latch 54 in a first position 58 relative to one another, first position 58 being when lever body 52 and lever latch 54 are clamped about housing pin 38; pivoting lever body 52 and lever latch 54 relative to one another and thereby positioning, selectively, lever body 52 and lever latch 54 in a second position 60 relative to one another, second position 60 being when lever body 52 and lever latch 54 are unclamped relative to housing pin 38. Lever body 52 includes a fork 64 having a first projection 66 and a second projection 68 which together form a first slot 70 therebetween which receives housing pin 38, second projection 68 of fork 64 having a reduced thickness relative to first projection 66 and being connected with proximal end 47 of elongate arm 18. Lever latch 54 includes a first hook 90 and a second hook 90, fork 64 being positioned between first hook 90 and second hook 90, first hook 90 and second hook 90 cooperating with fork 64 and first hook 90, second hook 90, and lever body 52 thereby clamping housing pin 38 when lever body 52 and lever latch 54 are in first position 58. Lever latch 54 includes a platform 86 and a boss 88 on platform 86, first hook 90 and second hook 90 extending from platform 86. Lever body 52 includes a hole 78, boss 88 extending through hole 78 when lever body 52 and lever latch 54 are in first position 58, boss 88 being at least partially retracted through hole 78 when lever body 52 and lever latch 54 are in second position 60.

Lever subassembly 10 includes a lever button 56, 256 which is slidably attached to lever body 52, the method including: (a) positioning, selectively, lever button 56, 256 in a first lever button position 96, first lever button position 96 being when lever button 56, 256 is attached to boss 88; and (b) positioning, selectively, lever button 56, 256 in a second lever button position 60, second lever button position 60 being when lever button 56, 256 is detached from boss 88. Boss 88 includes a head 92, lever button 56, 256 including a raceway 106, 306 that slidably receives head 92, lever button 56, 256 being in first lever button position 96 when head 92 is attached to raceway 106, 306. Lever body 52 includes a second slot 80, lever button 56 including a single downwardly depending projection 102 extending through second slot 80, downwardly depending projection 102 being moved in second slot 80 when lever button 56 is moved between first lever button position 96 and second lever button position 98, the broach handle assembly 10 being double offset. Lever button 256 includes two downwardly depending projections 302.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A medical instrument handle assembly for holding a medical instrument configured for preparing a bone to receive an implant, said medical instrument handle assembly comprising:
   a housing;
   a rigid housing pin stationarily fixed within said housing, said housing pin defining a pin axis;
   an elongate arm including a proximal end;
   a lever subassembly including a lever body and a lever latch, said lever body being pivotally connected to said proximal end of said elongate arm, said lever body and said lever latch being pivotally connected to one another and thereby being selectively positionable relative to one another between a first position and a second position, said first position being when said lever body and said lever latch are clamped about and contacting said housing pin, at least one of said lever body and said lever latch rotating about the pin axis to clamp about said housing pin, said second position being when said lever body and said lever latch are unclamped relative to said housing pin.

2. The medical instrument handle assembly of claim 1, wherein said lever body includes a fork having a first projection and a second projection which together form a first slot therebetween which receives said housing pin, said second projection of said fork having a reduced thickness relative to said first projection and being connected with said proximal end of said elongate arm.

3. The medical instrument handle assembly of claim 2, wherein said lever latch includes a first hook and a second hook, said fork being positioned between said first hook and said second hook, said first hook and said second hook cooperating with said fork and said first hook, said second hook, and said lever body thereby clamping said housing pin when said lever body and said lever latch are in said first position.

4. The medical instrument handle assembly of claim 3, wherein said lever latch includes a platform and a boss on said platform, said first hook and said second hook extending from said platform.

5. The medical instrument handle assembly of claim 4, wherein said lever body includes a hole, said boss extending through said hole when said lever body and said lever latch are in said first position, said boss being at least partially retracted through said hole when said lever body and said lever latch are in said second position.

6. The medical instrument handle assembly of claim 5, wherein said lever subassembly includes a lever button which is slidably attached to said lever body, said lever button being selectively positionable between a first lever button position and a second lever button position, said first lever button position being when said lever button is attached to said boss, said second lever button position being when said lever button is detached from said boss.

7. The medical instrument handle assembly of claim 6, wherein said boss includes a head, said lever button including a raceway configured for slidably receiving said head, said lever button being in said first lever button position when said head is attached to said raceway.

8. The medical instrument handle assembly of claim 7, wherein said lever body includes a second slot, said lever button including a single downwardly depending projection extending through said second slot, said downwardly depending projection configured for being moved in said second slot when said lever button is moved between said first lever button position and said second lever button position, the handle assembly being double offset.

9. The medical instrument handle assembly of claim 7, wherein said lever button includes two downwardly depending projections.

10. The medical instrument handle assembly of claim 1, wherein said housing defines a longitudinal axis and said pin axis is transverse to said longitudinal axis.

11. The medical instrument handle assembly of claim 1, wherein at least one of said lever body and said lever latch rotates about said pin axis to both clamp about said housing pin and unclamp from said housing pin.

* * * * *